(12) United States Patent
Yotsutsuji

(10) Patent No.: US 10,004,832 B2
(45) Date of Patent: Jun. 26, 2018

(54) SKIVED FILM FOR COVERING SURFACE OF PLUG FOR MEDICAL PURPOSES, PLUG FOR MEDICAL PURPOSES USING SAID FILM, PRE-FILLED SYRINGE USING SAID PLUG, AND METHOD FOR PRODUCING SAID FILM

(71) Applicant: COKI ENGINEERING INC., Osaka (JP)

(72) Inventor: Akira Yotsutsuji, Osaka (JP)

(73) Assignee: COKI ENGINEERING INC., Osaka (JP)

(*) Notice: Subject to any disclaimer, the term of this patent is extended or adjusted under 35 U.S.C. 154(b) by 389 days.

(21) Appl. No.: 14/988,186

(22) Filed: Jan. 5, 2016

(65) Prior Publication Data

US 2016/0129160 A1 May 12, 2016

Related U.S. Application Data (62) Division of application No. 14/117,791, filed as application No. PCT/JP2011/002836 on May 20, 2011.

(51) Int. Cl.
| | |
|---|---|
| B29C 43/56 | (2006.01) |
| B29C 43/00 | (2006.01) |
| B29K 27/18 | (2006.01) |
| A61L 31/04 | (2006.01) |
| A61M 5/31 | (2006.01) |
| A61M 5/315 | (2006.01) |
| A61L 31/06 | (2006.01) |
| A61M 5/32 | (2006.01) |
| B29D 7/01 | (2006.01) |
| B29K 105/00 | (2006.01) |

(52) U.S. Cl.
CPC ............ *A61L 31/048* (2013.01); *A61L 31/06* (2013.01); *A61M 5/31* (2013.01); *A61M 5/3129* (2013.01); *A61M 5/31513* (2013.01); *A61M 5/32* (2013.01); *B29D 7/01* (2013.01); *A61M 2005/3131* (2013.01); *B29K 2027/18* (2013.01); *B29K 2105/251* (2013.01)

(58) Field of Classification Search
None
See application file for complete search history.

(56) References Cited

U.S. PATENT DOCUMENTS

| | | | |
|---|---|---|---|
| 5,827,233 A | 10/1998 | Futagawa et al. | |
| 6,287,497 B1 * | 9/2001 | Kawachi | B29C 43/006 264/127 |
| 6,899,932 B1 * | 5/2005 | Ishiwari | B29C 43/006 264/108 |
| 2005/0118939 A1 | 6/2005 | Duescher | |

FOREIGN PATENT DOCUMENTS

| | | |
|---|---|---|
| CN | 101909675 A | 12/2010 |
| DE | 202008011890 U1 | 11/2008 |
| EP | 2226088 A1 | 9/2010 |
| JP | 06-287540 | 10/1994 |
| JP | 10-314305 | 12/1998 |
| JP | 2008260191 A | 10/2008 |
| JP | 2010142573 A | 7/2010 |
| JP | 2010201649 A | 9/2010 |
| WO | 2009084646 A1 | 12/2008 |

OTHER PUBLICATIONS

Office Action dated Oct. 12, 2017 from corresponding European Application No. 11866101.6.

* cited by examiner

*Primary Examiner* — Mary Lynn F Theisen
(74) *Attorney, Agent, or Firm* — Lucas & Mercanti, LLP (57) ABSTRACT

A method to make a PTFE skived film capable of exhibiting, with a single layer, sliding properties, barrier properties with regard to a liquid contact surface, and excellent tear resistance during injection molding. This skived film is obtained by cutting a polytetrafluoroethylene block or a modified polytetrafluoroethylene block subjected to a thermal fusion treatment under reduced pressure or subjected to a pressurized thermal fusion treatment after being subjected to fusion under reduced pressure.

8 Claims, 3 Drawing Sheets

SKIVED FILM FOR COVERING SURFACE OF PLUG FOR MEDICAL PURPOSES, PLUG FOR MEDICAL PURPOSES USING SAID FILM, PRE-FILLED SYRINGE USING SAID PLUG, AND METHOD FOR PRODUCING SAID FILM

CROSS REFERENCE TO RELATED APPLICATIONS

This application is a divisional application of U.S. patent application Ser. No. 14/117,791 filed Jan. 29, 2014, which was a '371 of PCT/JP2011/002836 filed May 20, 2011, the priority of both prior applications is claimed and both prior applications are incorporated by reference.

TECHNICAL FIELD

The present invention relates to a method for producing a polytetrafluoroethylene film suited as a covering film to be attached on a gasket of a syringe barrel that is used for administering a drug liquid to a human body or an animal in pharmaceutical and medical fields, or on an inner surface of an insertion bore formed in a top cap into which a tip end part of the syringe barrel for attachment of a needle is to be inserted, and further to a film produced by the method, and a plug for medical purposes and a pre-filled syringe using the film.

BACKGROUND ART

In pharmaceutical and medical fields, various plugs for medical purposes are used. Hereinafter, the technology concerning such plugs for medical purposes will be described with a pre-filled syringe in which such a plug for medical purposes takes a particularly important functional role, as an example.

Recently, a so-called pre-filled syringe has become frequently used. In the pre-filled syringe, a syringe barrel serving both as an injection cylinder and a drug liquid container is preliminarily filled with a drug liquid, and the syringe barrel is transported and stored in the condition that a tip end part to which a needle is to be attached is hermetically sealed with a top cap, and before administration of the drug liquid, a needle is attached to the tip end part of the syringe barrel from which the top cap has been removed, and then a piston rod (pushing rod) is pushed-in to slide the gasket toward the tip end of the syringe barrel, and thus the drug liquid in the syringe barrel is administered.

The pre-filled syringe is featured by the ability to administer a correct dose of a drug liquid without erroneous use of the drug liquid, non-necessity of a drug liquid transferring operation, and the ability to prevent microbial contamination of a drug liquid caused by the transferring operation.

In conventional pre-filled syringes made of resin, the gasket is made of vulcanized rubber or the like. For ameliorating the "poor sliding properties" when the rubber gasket slides on the inner surface of the syringe barrel, it is necessary to apply silicon grease on the surface of the gasket or on the inner surface of the syringe barrel, and decrease in titer due to adsorption of an active ingredient in the drug liquid by the silicon grease, and contamination of the drug liquid by silicon microparticles in the silicon grease and adverse effect thereof on a human body have been seen as problems. Also, there is a "problem with regard to a liquid contact surface" because a soluble ingredient in the rubber can elute into the drug liquid.

For solving these problems, a gasket in which a covering film formed of a polytetrafluoroethylene (hereinafter, also referred to as "PTFE") film is overlaid on the surface of a rubber gasket body has been developed. In such a gasket, the covering film formed of a PTFE film allows improvement in sliding properties of the gasket relative to the syringe barrel, and the like without use of silicon grease.

Here, as a method for producing a PTFE film which is to be a covering film, the following two methods are known: (1) following thermal pressure bonding of a laminate of at least two skived films obtained by cutting (skiving) a PTFE pressure-molded product, a thermal fusion treatment is conducted at a temperature higher than or equal to the melting point of PTFE to form a film (e.g., see Patent Literature 1), and (2) using a suspension containing PTFE resin powder, a dispersing agent, and a solvent as a material, a PTFE cast film having a center line mean roughness Ra of surface of 0.05 μm or less and a coefficient of kinetic friction of 0.2 or less is produced by a casting method (e.g., see Patent Literature 2).

By covering the surface of a gasket body with a covering film formed of a PTFE film produced by the foregoing methods, it is possible to improve the sliding properties of the gasket relative to the syringe barrel as described above, and to eliminate the need of applying silicon grease on the inner surface of the syringe barrel, thereby avoiding the aforementioned problems caused by the silicon grease.

Further, since the covering film is configured to be substantially water vapor impermeable by eliminating almost all of fine pinholes and fusion defective parts, it is possible to prevent a rubber ingredient (soluble ingredient) of the gasket body from leaching into the drug to contaminate the drug liquid. Therefore, the covering film can exert the aforementioned effect by being overlaid not only on the gasket for syringe where sliding properties are regarded as the most important properties, but also on a liquid contact inner surface of an insertion bore of a top cap for syringe into which a tip end part of the syringe barrel is to be inserted, or on a liquid contact surface of an insertion portion of a laminate rubber plug for vial, for its water vapor impermeability and barrier properties against a leached ingredient as described above.

CITATION LIST

Patent Literature

[PTL 1] Japanese Laid-Open Patent Publication No. 6-287540

[PTL 2] Japanese Laid-Open Patent Publication No. 10-314305

SUMMARY OF THE INVENTION

Problems to be Solved by the Invention

The conventional methods for producing a PTFE film has a problem of difficulty in efficiently and economically producing a PTFE film suited as a covering film. To be more specific, although a skived film obtained by cutting a block-shaped PTFE pressure-molded product allows efficient mass production of PTFE film at relatively low cost, the pressure-molded product formed by pressure molding of PTFE powder is a cluster of porous aggregates, and interspaces (interconnected cells) communicating with each other between PTFE powder particles forming the aggregates or along contact interfaces of neighboring aggregates in a weaving manner run all over the pressure-molded product in the form of a network. When such a porous pressure-molded product including interconnected cells is subjected to a thermal fusion treatment under normal pressure, the temperature of the block-shaped PTFE product subjected to the thermal fusion treatment rises from the superficial side, and contact interfaces of aggregates on the superficial side start fusing in first, and the fused area spreads, and eventually the entire surface of the superficial part is fused and the outlets of the interconnected cells are blocked and the gas is confined inside. This also applies to an aggregate wherein fusion starts on the superficial side previous to the inside, and the ambient gas is confined inside in the same manner. As a result, no matter if the temperature or the duration of the thermal fusion treatment is elevated or extended later, the confined gas will not be dissolved into the product subjected to the thermal fusion treatment, and will remain as closed cells. Hence, a skived film obtained by cutting such a product subjected to the thermal fusion treatment includes an infinite number of fine pinholes and fusion defective parts.

For making such a skived film into a covering film that is impermeable to water vapor, it is necessary to stack and integrate at least two skived films so that these fine pinholes and fusion defective parts are out of alignment as is in the forgoing former method. However, this method has a problem that process management and quality control are complicated because entirely new steps "stacking of films", "thermal pressure bonding", and "re-thermal fusion treatment" are added in order, compared to the case where a PTFE film is produced just by skiving.

Even if continuity of fine pinholes or fusion defective parts is broken by sticking a plurality of porous skived films together, an infinite number of pinholes still remain in the superficial skived film although the pinholes do not penetrate to the surface of the opposite side. When resin which is to become a plug body is injection molded for sticking the skived films on a sliding surface or a liquid contact surface of the plug body, the skived film may tear from one of the infinite number of pinholes as an origin due to impact elongation exerted on the skived films. This deteriorates the yield of molding.

On the other hand, in the latter method, the thickness of a PTFE film obtained by a single application is very small, and a film having a uniform thickness cannot be obtained unless the thickness of the film is gradually increased by repeating a series of steps of "application of PTFE suspension", "drying", and "thermal fusion treatment" for obtaining a film having a thickness of about 20 μm to 150 μm which is particularly suited as a covering film. Therefore, the production efficiency is very poor, and there is a problem of difficulty in economically producing a PTFE cast film suited as a covering film.

Additionally, since a PTFE suspension is used for application, an infinite number of pinholes occur in the dry film as the suspension gradually gets dry, and the pinholes remain even after the dry film is subjected to a thermal fusion treatment. Then, films are piled up by repeated application, drying, and a thermal fusion treatment, and pinholes occurring in the respective films are out of alignment and do not communicate with each other. Therefore, a PTFE cast film having excellent water impermeability and barrier properties comparable with those described above is formed. However, since pinholes appear in films of front and back superficial layers, tear can be caused from one of these pinholes as an origin, during injection as described above.

Therefore, it is a primary object of the present invention to provide a PTFE skived film capable of exhibiting, with a single layer, sliding properties, barrier properties relative to a liquid contact surface, and excellent tear resistance during injection molding which are the aforementioned problems, and a method for producing the film. It is a secondary object of the present invention to provide a plug for medical purposes and a pre-filled syringe produced efficiently and economically by using the PTFE film produced by said method.

Solution to the Problems

A first aspect is characterized by "a skived film for covering a surface of a plug for medical purposes obtained by cutting a polytetrafluoroethylene block or a modified polytetrafluoroethylene block subjected to a thermal fusion treatment under reduced pressure or subjected to a pressurized thermal fusion treatment after being subjected to fusion under reduced pressure", and a second aspect is characterized in that "tensile elongation in a machine direction which is a longitudinal direction of the film is greater than or equal to 500%".

A conventional skived film can hardly be used for covering a surface of a plug for medical purposes because it includes an infinite number of pinholes and fusion defective parts as described above, and has "water vapor impermeability" much lower than that required for medical purposes. In contrast, as will be described later, the film obtained by cutting a product subjected to a "thermal fusion treatment under reduced pressure", or "pressurized thermal fusion treatment after being subjected to fusion under reduced pressure" includes no fine pinholes and fusion defective parts, and satisfies the water vapor impermeability (amount of water vapor transmission is measured for determination) required for covering surface of a plug for medical purposes, so that it first finds application as a film for covering a surface of a plug for medical purposes. Also when "tensile elongation in a machine direction which is a longitudinal direction of the film is greater than or equal to 500%", impact elongation in covering an elastomer for a plug body during the injection molding step is overcome and the film will not tear, so that it is possible to realize such high yield in injection molding that cannot be achieved by a cast film or by a conventional skived film. Since the skived film is stretched in the longitudinal direction when it is passed through a roller under tension for removing the undesired curling, elongation is smaller in the longitudinal direction than that in the width direction. Therefore, elongation occurs in the machine direction which is a longitudinal direction.

In a plug for medical purposes described in a third aspect, for example, a gasket for syringe, an intermediate gasket for syringe, a top cap for syringe, or a laminate plug for vial as described in a fourth aspect, or a pre-filled syringe described in a fifth aspect, since the skived film according to the first or second aspect is overlaid on the superficial surface, or at least on the sliding surface or the liquid surface of the plug body made of elastomer, it is possible to realize smooth movement of a piston, and to block elution of an inhibitor from the elastomer on the body side to the drug liquid side in the liquid contact part, and to block water diffusion from the charged drug liquid by exertion of "sliding properties", "barrier properties", and "water vapor impermeability".

According to a sixth aspect, a method for producing a polytetrafluoroethylene film for covering a surface of a plug for medical purposes (first method) is characterized by the steps of "pressure-molding powder material of polytetrafluoroethylene or modified polytetrafluoroethylene charged in a mold to obtain a pressure-molded product having interconnected cells inside; subjecting the pressure-molded product obtained by the pressure molding to a thermal fusion treatment under reduced pressure; and cutting the product subjected to the thermal fusion treatment obtained by the thermal fusion treatment to obtain a film".

Here, "subjecting the pressure-molded product obtained by the pressure molding to a thermal fusion treatment under reduced pressure" means that the ambient pressure has reached (or almost reached) a reduced pressure condition before "heating" the pressure-molded product for "fusion treatment" as will be described in detail later. And this "reduced pressure condition" is kept until at least the entire superficial surface of the pressure-molded product is baked into the state including practically no pinhole (the entirety is covered with a skin). By keeping the reduced pressure until the superficial surface is baked to the state including practically no pinhole, the pressure-molded product is baked to the state where no pinholes are included up to the core by preventing the external air from entering the pressure-molded product undergoing thermal fusion even if the ambient pressure is returned to normal pressure later. Of course, pressure reduction may be continued until thermal fusion completes or cooling completes.

Next, the "fusion treatment" will be described. PTFE powder charged in a mold is pressure-molded to form a pressure-molded product, and the pressure-molded product is a block of a predetermined shape formed by assembly of aggregates which are clusters of fine powder particles.

As is described in the section of PROBLEM, an aggregate is made up of fine powder particles which are in contact with each other, and is a porous aggregate in which networks of fine communication holes run. Also in a pressure-molded product which is a cluster of the aggregates, the parts that cannot properly come into contact with each other in the vicinity of contact interfaces between aggregates form coarse interspaces (interconnected cells), and networks of these coarse interconnected cells run throughout the interior of the pressure-molded product as is the same with the above. Therefore, it is doubly porous.

By reducing the pressure to a predetermined pressure before starting heating of the "fusion treatment", not only the coarse interspaces (interconnected cells) remaining between aggregates as described above are drawn outside, but also the gas having entered inside the interconnected cells during the compression molding is drawn outside from the fine interconnected cells remaining in the aggregates (degassed), so that the interior has the same (almost the same) reduced pressure condition as that of the ambient environment.

When "heating" for the "fusion treatment" is started in this condition, contact interface between neighboring aggregates softens by the heat and fusion gradually progresses from the superficial side of the pressure-molded product toward the interior. At the same time, also in the aggregates residing in the superficial part of the pressure-molded product, softening and fusion gradually progress from the superficial side. As a result, softening and fusion progress even in the aggregates residing on the superficial side of the pressure-molded product, prior to the interior. Therefore, bubbles that have turned into closed cells from the interconnected cells because of closure of the outlets are left inside.

In association with progression of thermal fusion (or temperature elevation or keeping of fusion temperature), the fused area gradually extends due to reduction in surface tension at contact interface, and the closed cells are reduced. At this time, since the internal pressure of the closed cells is reduced and there is little gas in the interior, and there is no resistance that interferes extension of fusion, the closed cells can be reduced to the minimum, and occurrence of fine pinholes and fusion defective parts inevitably accompanying a powder thermal fusion treatment is greatly controlled. Such fusion also occurs inside aggregates as well, and substantially complete fusion is achieved in the entire product subjected to the thermal fusion treatment. And at the time when fusion has progressed to the core, the "fusion treatment" completes and cooling follows.

By producing a film by cutting a product subjected to the thermal fusion treatment obtained by such a thermal fusion treatment method, it is possible to obtain a PTFE film including least fine pinholes and fusion defective parts, that is substantially water vapor impermeable and suited as a covering film.

A seventh aspect is further improvement of the sixth aspect (second method), and characterized by the steps of "pressure-molding powder material of polytetrafluoroethylene or modified polytetrafluoroethylene charged in a mold to obtain a pressure-molded product having interconnected cells inside; subjecting the pressure-molded product to a primary thermal fusion treatment under reduced pressure to block outlets of communication holes of the pressure-molded product to obtain a product subjected to the primary thermal fusion treatment including only closed cells remaining inside; subjecting the product subjected to the primary thermal fusion treatment to a secondary thermal fusion treatment under increased pressure to obtain a product subjected to the secondary thermal fusion treatment from which the closed cells have disappeared; and cutting the product subjected to the secondary thermal fusion treatment to obtain a film".

Also in this case, the "primary thermal fusion treatment" is started in the condition that the pressure is reduced to an approximately predetermined pressure. And, the product subjected to the primary thermal fusion treatment in which apertures of fine communication holes in aggregates located in the superficial part of the pressure-molded product or coarse communication holes between aggregates are closed and only closed cells having reduced internal pressure remain as a result of the primary thermal fusion treatment, is subjected to the secondary thermal fusion treatment under increased pressure. Since the entire superficial surface of the product subjected to the primary thermal fusion treatment is covered with a skin, the pressure is applied on the entire superficial surface of the product subjected to the primary thermal fusion treatment, and the entirety is pressed toward the center, and the closed cells gradually disappear by this pressurization force without any resistance.

In the first method not employing "pressurization", fusion progresses only by reduction in surface tension at contact interface "during fusion". When the closed cells gradually contract to become very fine pinholes, such fine pinholes are physically crushed by "pressurization" although they are difficult to be eliminated only by reduction in surface tension. Hence, the product subjected to the secondary thermal fusion treatment is much denser than the product subjected to the thermal fusion treatment produced by the first method. By preparing a film by cutting the product subjected to the secondary thermal fusion treatment obtained in such a manner, it is possible to obtain a PTFE film that includes lesser fine pinholes and fusion defective parts, and is more impermeable to water vapor and more desirable as a covering film than the film formed in the invention described in the sixth aspect. Shifting from the primary thermal fusion treatment to the secondary thermal fusion treatment may be conducted continuously using the same thermal fusion treatment furnace, or the treatments may be conducted in a batch manner using different thermal fusion treatment furnaces.

Powder material of PTFE used herein is powder of solely PTFE, and modified PTFE is PTFE that is modified for adaptation to the use. In the present invention, elongation is an important factor as will be described later, and hence, modified PTFE in which priority is given to elongation, for example, a polymer of tetrafluoroethylene obtained by copolymerizing 0.01 to 1 part by weight of alkylvinylether having one to four carbon atoms in a perfluoroalkyl chain with 100 parts by weight of PTFE is recited as an example.

Here, the pressure in reducing the pressure during the thermal fusion treatment (or the primary thermal fusion treatment) preferably falls within the range of 0.013 to 133 Pa. When the pressure (reduced pressure) during the thermal fusion treatment is higher than 133 Pa (or the degree of vacuum is lower than the predetermined range), degassing of the gas having entered interspaces between neighboring PTFE aggregates as well as in fine pinholes in PTFE aggregates is insufficient, and the gas is confined inside during the thermal fusion treatment, so that fine pinholes and fusion defective parts remain. On the contrary, when the pressure is lower than 0.013 Pa (or the degree of vacuum is higher than the predetermined range), gas does not remain not only in interspaces between neighboring PTFE aggregates but also in fine pinholes in PTFE aggregates, however, massive equipment is required for generating vacuum and it is no longer possible to efficiently and economically obtain the product subjected to the thermal fusion treatment (or product subjected to the primary thermal fusion treatment). In short, the reduced pressure is selected so that fine pinholes and fusion defective parts will not remain in the product subjected to the thermal fusion treatment (or the product subjected to the primary thermal fusion treatment).

An eighth aspect is characterized in that "the powder material of polytetrafluoroethylene or modified polytetrafluoroethylene charged in the mold is pressure-molded under reduced pressure to obtain a pressure-molded product" in the sixth and seventh aspects, and according to this, it is possible to obtain a pressure-molded product having a much higher density than that obtained by pressure-molding at normal temperature.

In the method for producing a polytetrafluoroethylene film, it is preferred that "a thermal fusion treatment temperature (or primary, secondary thermal fusion treatment temperature) is 320 to 400° C.". Since the melting point of PTFE is approximately 327° C. (gelation occurs and mechanical properties rapidly change at temperatures higher than this), a longer time is required for the thermal fusion treatment when the temperature during the thermal fusion treatment is less than 320° C. On the contrary, since the temperature at which PTFE starts decomposing is approximately 390° C., decomposition starts and gas bubbles occur inside the fused product when the temperature during the thermal fusion treatment exceeds 400° C. In view of the melting point of PTFE, the temperature is more preferably 350 to 370° C. at which fusion easily progresses, and within this temperature range, the shape will not be lost upon heating at a temperature exceeding the melting point, and the shape will be restored without deterioration upon returning to normal temperature.

The pressurization pressure during the secondary thermal fusion treatment is higher than or equal to 0.2 MPa. Generally, when the thermal fusion treatment temperature is low, the pressurization pressure is set high, and when the thermal fusion treatment temperature is high, the pressurization pressure is set low. Of course, when both of these are set high, the thermal fusion treatment is accelerated. When the pressure is lower than 0.2 MPa, the method does not differ from the first method. The higher the pressurization force, the more the tensile elongation (%) and the amount of water vapor transmission are improved, however, pressurization at 5 MPa or higher is not economical because an extra cost is required for the pressure resistant structure of the pressurized heating furnace. Therefore, the upper limit is practically 5 MPa.

While the shape of the product subjected to the thermal fusion treatment (or the product subjected to the secondary thermal fusion treatment) is not specified, it is preferably "a rectangular parallelepiped or a cube" or "a circular column or a cylinder". In the case of a cylinder, in particular, fusion progresses both from the superficial side and the inner side, and fusion progresses rapidly and completely to the core. In the case of "a rectangular parallelepiped or a cube", a film of a required size can be obtained by planing, and in the case of "a circular column or a cylinder", a long PTFE film can be produced efficiently and economically by passing a mandrel in the center, and cutting the product subjected to the thermal fusion treatment (or the product subjected to the secondary thermal fusion treatment) while it is rotated circumferentially about the mandrel.

It is preferred that "the film obtained by cutting the product subjected to the thermal fusion treatment (or the product subjected to the secondary thermal fusion treatment) has a thickness ranging from 20 to 150 μm". A film having large thickness is used for deep drawing.

Here, "elastomer" is a generic name for materials having rubber-like elasticity, and includes both "thermosetting elastomer" generally called "rubber" having relatively high heat resistance that will not soften upon application of heat such as vulcanized rubber and thermosetting resin elastomer, and "thermoplastic elastomer" that will soften to exhibit fluidity upon application of heat, and return to a rubber-like elastic body upon cooling, and can be rapidly formed by injection molding.

Examples of the "drug container" include "syringe" and "vial". Specific examples of the "plug for medical purposes" include a gasket for syringe, an intermediate gasket for syringe, a top cap for syringe, and a laminate plug for vial (the fourth aspect).

The invention described in the fifth aspect of the present invention is a pre-filled syringe featured in that "the syringe barrel 4 charged with the drug liquid 7 is hermetically sealed with the gasket for syringe 1 and the top cap for syringe 6 as exemplified in the fourth aspect".

Advantageous Effects of the Invention

According to the present invention, by developing a novel skived method and employing the same, application of a skived film as a covering film for a plug for medical purposes, that has been conventionally considered to be impossible, is enabled. As a result, it becomes possible to efficiently and economically provide a plug for medical purposes such as a gasket for syringe and a pre-filled syringe by using the PTFE film produced by this method.

DESCRIPTION OF EMBODIMENTS

Figure 1:
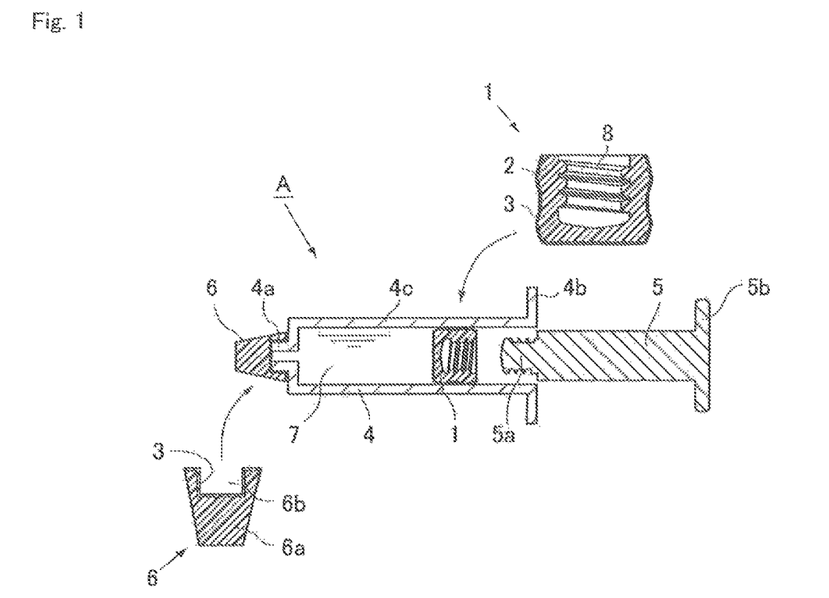
FIG. 1 is a cross-sectional view showing one example of a pre-filled syringe to which the present invention is applied.

Hereinafter, for example, a pre-filled syringe (of course the one to which the PTFE skived film of the present invention is applied, but not limited to a pre-filled syringe) to which the present invention is applied, and a PTFE skived film used in the pre-filled syringe will be described with reference to the drawings. FIG. 1 is a cross-sectional view showing one example of a pre-filled syringe A (of the present invention) to which a gasket for syringe 1 and a top cap for syringe 6 which are plugs for medical purposes of the present invention are applied.

As shown in FIG. 1, the pre-filled syringe A of the present invention generally includes the gasket for syringe 1 (hereinafter, also referred to simply as "gasket 1"), a syringe barrel 4, a piston rod 5, and the top cap for syringe 6 (hereinafter, also referred to simply as "top cap 6"). Reference numeral 7 in FIG. 1 denotes a drug liquid (injection liquid) charged in the syringe barrel 4.

As shown in the enlarged view of FIG. 1, the gasket 1 includes a gasket body 2, and a skived film 3 for covering formed of a polytetrafluoroethylene (PTFE) film overlaid to entirely cover a sliding surface relative to the inner surface of the syringe barrel 4, and a liquid contact surface in the gasket body 2.

The gasket body 2 is an approximately circular columnar member (namely, plug body) formed of elastomer, having a diameter of the center part slightly smaller than diameters of the lateral sides, and is provided in its bottom surface (surface on the side to which the piston rod 5 is attached) with a female screw portion 8 for connecting the piston rod 5.

The "elastomer" forming the gasket body 2 includes both "thermosetting elastomer", such as vulcanized rubber and thermosetting resin elastomer, and "thermoplastic elastomer" as described above.

Examples of the vulcanized rubber include butyl rubber, SBR (styrene-butadiene rubber), EPR (ethylene-propylene rubber), EPDM (ethylene-propylene-diene rubber), NBR (acrylonitrile butadiene rubber), NR (natural rubber), IR (isoprene rubber), CR (chloroprene rubber), IIR (butyl rubber), chlorinated butyl rubber, and brominated butyl rubber, and examples of the thermosetting resin elastomer include fluorine rubber and silicone rubber.

Examples of the thermoplastic elastomer include SBS (styrene-butadiene-styrene block copolymer), SEBS (styrene-ethylene-butadiene-styrene block copolymer), EP (ethylene-propylene copolymer), PA (polyamide), and polyurethane.

Figure 3:
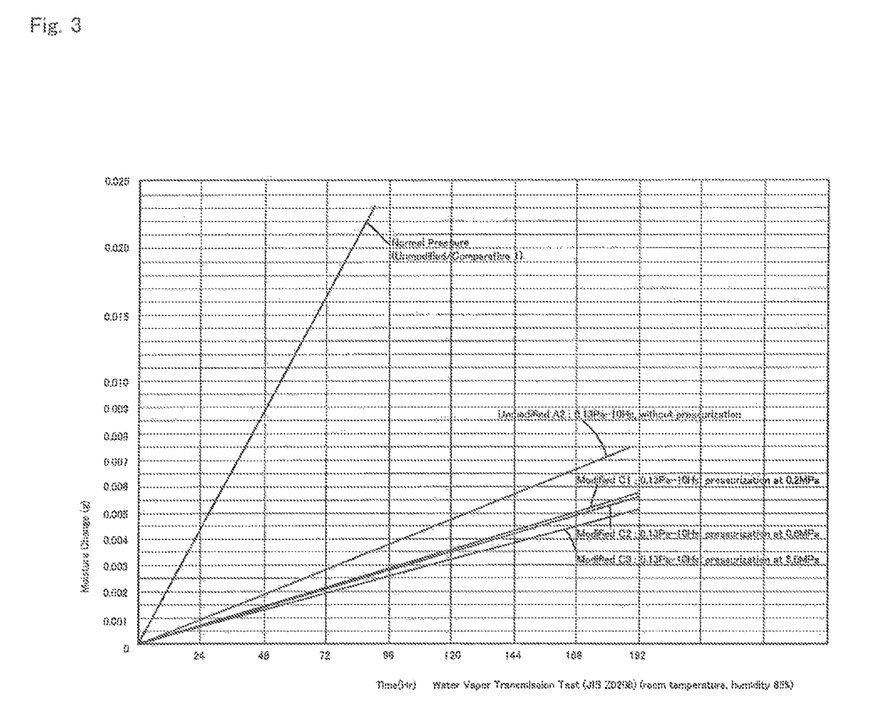
FIG. 3 is a graph for comparing results of a water vapor transmission test for skived films prepared by a normal pressure fusion method and the first and second methods of the present invention.

The covering film 3 is formed of the PTFE film obtained by the skived method according to the present invention, and contains in the entire film, almost no fine pinholes which are residues of interspaces between aggregates and fine pinholes included in the aggregates, as well as porous aggregates that are observed in the state of the pressure-molded product (see the result of the water vapor transmission test in Table 1 and FIG. 3). Although tensile elongation (%) differs in the longitudinal direction (machine direction) and in the width direction (cross direction) of the film as described above, the film has enough resistance to later-described impact elongation to endure impact elongation during injection of the gasket body 2 even in the longitudinal direction of the film in which tensile elongation (%) is smaller (see results of elongation test in Table 1), and tear of the film during injection is hardly observed. The surface of the PTFE film obtained by the skived method according to the present invention has an infinite number of very shallow parallel knife cuts that are formed during cutting in the longitudinal direction of the film, however, since the infinite number of very shallow knife cuts run in the longitudinal direction of the film having smaller tensile elongation (%), the knife cuts will not become an origin of tear during injection molding, and there is no pit (hole) in the surface that is to become an origin of tear inevitable for a cast film.

The skived film as described above is overlaid to entirely cover the sliding surface relative to the inner surface of the syringe barrel 4 (in other words, outer circumferential face of the gasket body 2) and the tip end surface which is a liquid contact surface in the gasket body 2, to impart high sliding properties to the sliding surface of the gasket body 2, and barriers properties of inhibiting transfer of a water-soluble impurity into the drug liquid from the gasket body 2 and water vapor impermeability of preventing evaporation of water from the charged drug.

Preferably, the thickness of the PTFE film forming the covering film 3, before being overlaid on the gasket body 2, ranges from 20 μm to 150 μm, inclusive. The film thickness is selected depending on the shape of the material to be laminated, in particular, depending on the deep drawing amount. A thicker film is used for a deeper drawing amount.

Since the syringe barrel 4 has many variations from a small-sized one having a small inner diameter (for example, an inner diameter of 4.65 mm) to a large-sized one having a large diameter (for example, an inner diameter of 50 mm) for imaging, the gasket 1 itself also has corresponding variations from one having a small diameter to one having a large diameter, and also the film thickness of the covering film 3 used herein is selected depending on the shape and the depth of drawing.

Figure 4:
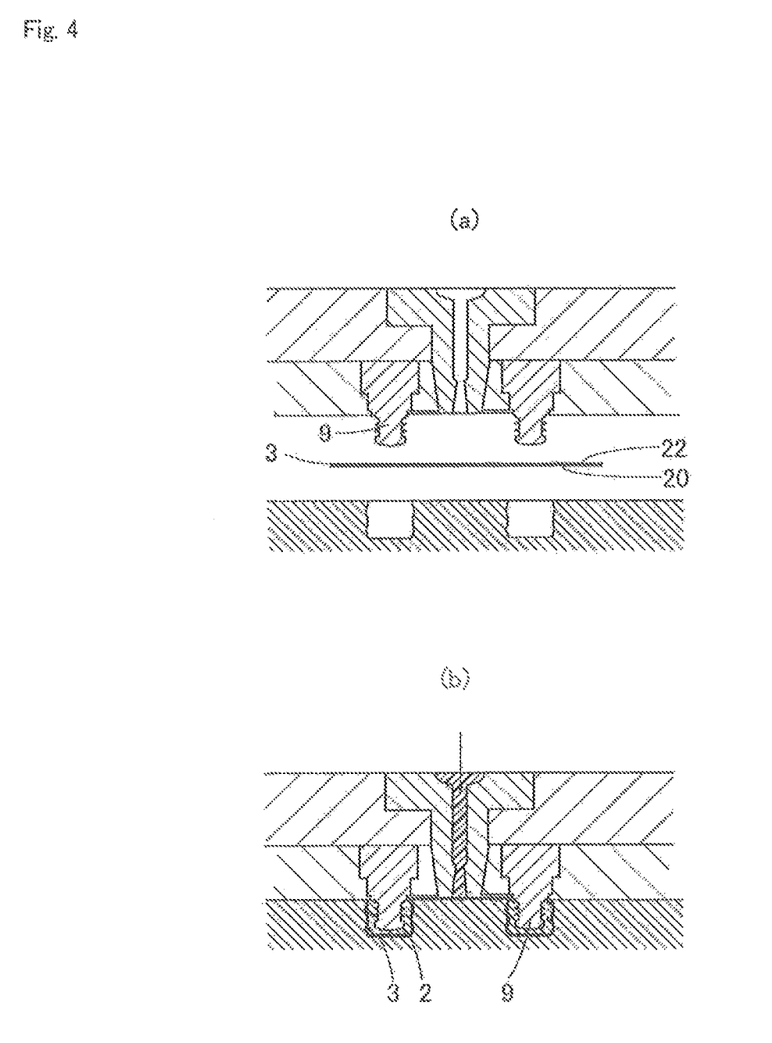
FIG. 4 is a cross-sectional view of major part showing one example of a method for attaching a film to a gasket body in a stretched manner.

Lamination of the covering film 3 onto the gasket body 2 is achieved by injection molding carried out in the following manner. The covering film 3 is stretched on a female mold in which the shape of the gasket is engraved, then a male mold having a male screw portion 9 formed in a protruding manner for screw attachment of a piston rod is set to push the covering film 3 into the bore for forming a gasket in the female mold, and an elastomer which is to become the gasket body 2 is charged at high speed by being injected at high pressure between the pushed-in covering film 3 and the male screw portion 9 (see FIG. 4).

In such injection molding, the covering film 3 is rapidly stretched in the machine direction and the cross direction of the film by injection of the elastomer at high pressure, and elongation is a very important factor in mass production because poor elongation may cause tear. A thick film is used for deep drawing because it allows large elongation. At the same time, it is also important to improve the elongation of the covering film 3 for enduring injection at high pressure as is already described, and for this, it is more preferred to produce and use, in place of the PTFE film, a modified PTFE film by using modified PTFE (for example, a polymer of tetrafluoroethylene obtained by copolymerizing 0.01 to 1 part by weight of alkylvinyl ether having 1 to 4 carbon atoms in a perfluoroalkyl chain with 100 parts by weight of PTFE) as powder material.

Regarding the elongations of these films (in particular, modified PTFE film), these films preferably exhibit tensile elongation (more strictly, fracture elongation) of at least 500% or greater in the machine direction in which the film is weak (As described above, since the skived film is passed between multi-stage rollers under tension in the longitudinal direction for eliminating waving of the film after being formed into a film by cutting, the film is stretched in the longitudinal direction of the film and thus has higher tensile strength in the longitudinal direction than in the width direction, but elongation in the longitudinal direction is deteriorated in comparison with that in the width direction.). The tensile elongation in the longitudinal direction of the sample shown in Table 1 that is likely to cause tear of film during injection molding (Unmodified/Comparative 1 (Comparative example: Film fused at atmospheric pressure without pressure reduction and pressurization, using unmodified material)) is 450%.

With the elongation in the machine direction of less than or equal to 500%, the PTFE film may tear depending on the shape of the gasket 1 during stretching in injection molding of the gasket 1. While an upper limit of elongation is not limited, excessive elongation makes the film too soft to impair not only sliding properties but also shape retention of the gasket 1, although large elongation will not inhibit resilience of the gasket body 2. From this point of view, preferably, an upper limit of elongation is practically 650% or 700%. Thus, the thickness of the PTFE film or the modified PTFE film overlaid on the gasket body 2 by injection is 10 μm to 20 μm. And knife cuts in the shapes of fine projecting and recessed lines generated by cutting are significantly lessened to such a degree that they will disappear by the great elongation during injection molding as described above. An adhesion surface of the covering film 3 with regard to the gasket body 2 is subjected to an adhesiveness improving treatment as will be described later for enhancing adhesiveness.

The method for producing a PTFE skived film that forms the covering film 3 described hereinafter is an improved method based on a conventional skiving method. Specifically, first, powder material (so-called molding powder) of polytetrafluoroethylene (PTFE) or modified PTFE is charged in a mold, and compressed at room temperature, under a pressure of 10 to 50 MPa to form a circular columnar or cylindrical product. The pressure at the time of compression is limited in the above range because when the pressure is lower than 10 MPa, mechanical strength of the obtained pressure-molded product is poor, and the handling such as transfer to the subsequent step becomes difficult, and a lot of air remain inside the pressure-molded product, so that fine pinholes and fusion defective parts frequently occur in the obtained film when the pressure-molded product is finally processed into a film. When the pressure is higher than 50 MPa, the mechanical strength of the pressure-molded product is improved, but the problem of fine pinholes or fusion defective parts in the obtained film remains unsolved, and the properties of the film are not so improved although the massive equipment for pressurization is used. (Here, the pressure-molded product can be further densified by employing pressure reduction together with compression under pressurization. The pressure reduction may be employed after compression molding under pressurization. When the reduced pressure condition can be maintained continuously to the subsequent fusion treatment, it is convenient to shift to the fusion treatment while keeping the reduced pressure condition to avoid the need of reducing the pressure again in the fusion treatment.) This point also applies to the second method. The degree of pressure reduction is preferably 0.013 to 133 Pa for adaptation to the subsequent step.

The shape of the pressure-molded product is not particularly limited, and an optimum shape such as a circular column, a cylinder, a rectangular parallelepiped or a cube is selected depending on the method for forming a film from the product subjected to the thermal fusion treatment and on the thermal fusion treatment condition. The pressure-molded product is a cluster of aggregates of PTFE powder material or modified PTFE powder material because it is formed just by compression under pressurization. Therefore, there are an infinite number of interspaces of various sizes between neighboring powder particles or between neighboring aggregates although powder particles inside each aggregate adhere tightly to each other, and the aggregates adhere tightly to each other at their contact interface. The interspaces communicate with each other to give a network of fine communication holes throughout the pressure-molded product, so that the pressure-molded product is porous. When the pressure-molded product is put in a reduced pressure condition, and this condition is not maintained, these communication holes are filled with gas in the ambient environment (normally air).

Then, the pressure-molded product formed in an atmospheric pressure is put into a heating furnace, and the internal pressure of the heating furnace is reduced to a degree of vacuum of 0.013 to 133 Pa, and the interior of the pressure-molded product accommodated in the furnace is also made to have the same degree of vacuum to remove the gas from the interspaces (communication holes). Typically used degree of vacuum ranges from 0.13 Pa to 13.3 Pa. After conducting the thermal fusion treatment as described above, normally at 320 to 400° C. (more preferably 350 to 370° C.) for several to several ten hours, depending on the size and the shape of the pressure-molded product while keeping this reduced pressure condition, the pressure-molded product is cooled to obtain a product subjected to the thermal fusion treatment.

In the pressure-molded product undergoing the thermal fusion treatment, since the temperature rises from the superficial side, and the heat is conducted toward the center part, fusion of PTFE aggregate itself and fusion at contact interfaces between aggregates progress from the superficial side in an early stage of the thermal fusion treatment in the porous pressure-molded product, and the aforementioned interspaces gradually disappear. On the other hand, inside the aggregates themselves and inside the pressure-molded product which is a cluster of the aggregates, fusion at contact interface is delayed, and interspaces are confined inside because temperature rise is delayed. In other words, outlets of interconnected cells are blocked to give closed cells.

However, fusion at contact interface is not interfered because there is little gas inside the interspaces (closed cells), and disappearance of interspaces (closed cells) up to the core of the pressure-molded product is eventually achieved. By securing a sufficient thermal fusion treatment time, fusion at contact interface completely progresses, and elimination of fusion defective parts due to defective fusion is also achieved. Therefore, an estimated duration and heating temperature of the thermal fusion treatment is the time required for fine pinholes and fusion defective parts inside the product subjected to the thermal fusion treatment to disappear, from the purpose of producing a PTFE film with no fine pinholes, which is an object of the present invention.

Here, the pressure reduction range in reducing the internal pressure of the heating furnace during the thermal fusion treatment is preferably 0.013 to 133 Pa as described above. Further, the temperature during the thermal fusion treatment is preferably in the range from 320 to 400° C. (more preferably 350 to 370° C.) as described above. Technical significances of the pressure range and the temperature during the thermal fusion treatment are as described above. As an indication for the thermal fusion treatment, although fusion is expected to progresses to the core typically in about five hours after the temperature has reached a predetermined temperature (360° C.) for a circular columnar product having an outer diameter of 100 mm, an inner diameter of 20 mm, and a thickness of 40 mm, heating is conducted for about ten hours for safety and then cooling by allowing to cool follows.

As another method for obtaining a product subjected to the thermal fusion treatment (second method), the following method may be employed. Specifically, similarly to the first method, powder material of polytetrafluoroethylene or modified polytetrafluoroethylene is charged in a mold, and pressure-molded under normal pressure or reduced pressure to obtain a pressure-molded product. The pressure molding and the formed shape are as same as those in the first method.

Then, the pressure-molded product is subjected to a primary thermal fusion treatment under reduced pressure. The condition of the thermal fusion treatment is as described above, and interspaces (interconnected cells) are blocked from the superficial side of the pressure-molded product. In this case, an estimated duration of the primary thermal fusion treatment is the time required for communication holes in the entire surface on the superficial side of the product subjected to the primary thermal fusion treatment to disappear to give the condition that only closed cells remain inside. The thermal fusion treatment temperature is as same as that in the first method.

After conducting the primary thermal fusion treatment, the product subjected to the primary thermal fusion treatment is subjected to a secondary thermal fusion treatment under increased pressure by pressurizing the interior of the same heating furnace to a predetermined pressure, or by taking out the product subjected to the primary thermal fusion treatment and transferring it to another heating furnace, and pressurizing the interior of the heating furnace to a predetermined pressure.

The secondary thermal fusion treatment is conducted under increased pressure because the entire surface of the superficial part of the product subjected to the primary thermal fusion treatment is fused, and the pressurization force in the thermal fusion treatment furnace is exerted toward the center from the entire superficial surface of the product subjected to the primary thermal fusion treatment, to crush the closed cells remaining inside under reduced pressure. At the same time, contact interface of powder particles forming PTFE aggregates themselves that are physically in contact with each other, and contact interface of the aggregates are fused by the heat transferred from the superficial side, and almost all of the remaining fine pinholes and fusion defective parts are eliminated. In the second method, since the secondary thermal fusion treatment is conducted under increased pressure, elimination of fine pinholes and fusion defective parts is achieved more completely up to the core. The thermal fusion treatment temperature is as same as that in the primary thermal fusion treatment.

The pressurization pressure in the secondary thermal fusion treatment is higher than or equal to 0.2 MPa (practically, the upper limit is 5 MPa as described above). Normally, the pressurization pressure is raised when the thermal fusion treatment temperature is low, and the pressurization pressure is lowered when the thermal fusion treatment temperature is high. For shortening the fusion time, the temperature and the pressure are raised. The technical significance of the pressurization range is as already described. A practical pressurization range is 0.7 to 0.9 MPa.

Then, the product subjected to the thermal fusion treatment obtained by the first method or the product subjected to the secondary thermal fusion treatment obtained by the second method is set, for example, on a lathe machine while a mandrel is passed through the center hole thereof when the product is of a cylindrical shape, and rotated circumferentially, and in this condition, a cutting tool such as metallic knife is pushed at a specific angle at a specific pressure to cut the product to obtain a PTFE film of 20 to 150 μm thick. When the product subjected to the thermal fusion treatment or the product subjected to the secondary thermal fusion treatment is a cylindrical solid, after cutting out the center part of the product, a mandrel is passed therethrough as described above, or press-fitted therein, and then the product is subjected to cutting. When the product is a rectangular parallelepiped or a cube, a PTFE film is obtained by a method like planing. The obtained film is passed through a roller under heating to remove the undesired curling occurring by cutting (rotary cutting). As a result, the film is stretched and has slightly higher tensile strength in the rolling direction (or the longitudinal direction of the film or the machine direction) than in the width direction (cross direction), while on the other hand, it has smaller elongation in the machine direction than in the cross direction.

In the film obtained in this manner, PTFE powder particles in aggregates themselves and neighboring aggregates are fused and integrated in a seamless manner as if rice cakes were fused, and very little fine pinholes and fusion defective parts that may cause tear of the film during injection molding are included in the superficial surface, although the superior surface includes microscopic knife cuts in the longitudinal direction of the film. Therefore, it becomes possible to efficiently and economically produce a PTFE film that is substantially impermeable to water vapor and is desirable as a covering film. As described above, microscopic knife cuts are not disadvantageous in injection molding.

The PTFE film produced in the manner as described above has essentially poor adhesiveness, and is disadvantageous in that the joining strength with the gasket body 2 is very weak. For this reason, it is necessary to apply an "adhesiveness improving treatment" on the joint surface between the PTFE film and the gasket body 2. In the present embodiment, the "adhesiveness improving treatment" is conducted by providing the joint surface between the PTFE film and the gasket body 2 with a silica microparticle layer made up of a binder and silica ($SiO_2$) microparticles (not shown), to allow secure joining between the PTFE film having poor adhesiveness and the gasket body 2 mainly by the anchoring effect. Of course, as the "adhesiveness improving treatment", other methods such as a chemical treatment with metallic sodium or a plasma treatment in an argon atmosphere may be conducted in place of the above method. In FIG. 4(a), the surface subjected to the adhesiveness improving treatment of the PTFE skived film 3 is denoted by 22, and the surface not subjected to the treatment is denoted by 20.

The syringe barrel 4 is formed with a needle attachment part 4a in its tip end, a finger hook part 4b in its rear end, and a cylindrical drug liquid packing part 4c therebetween, and is made of cyclic polyolefin in this embodiment. Of course, the shape of the syringe barrel 4 is not limited to the depicted one, and the syringe barrel 4 may be made of polypropylene, glass, or the like.

The piston rod 5 is a rod-like member having a gasket attachment part 5a in its tip end part, and a finger rest part 5b in its rear end. The outer circumference of the gasket attachment part 5a of the piston rod 5 is engraved with a male screw to be screwed with the female screw portion 8 formed by digging the gasket body 2 of the gasket 1 as described above. Also, the piston rod 5 is formed of a resin such as cyclic polyolefin, polycarbonate, or polypropylene, similarly to the aforementioned cylinder 4.

The top cap 6 is a sealing member that is attached to the needle attachment part 4a of the syringe barrel 4 to prevent the drug liquid 7 charged in the syringe barrel 4 from leaking, and to prevent the drug liquid 7 from being contaminated by bacteria and so on suspended in the air. The top cap 6 is made up of an approximately circular columnar cap body (or plug body) 6a, and the covering film 3 overlaid in the same manner for the gasket 1, on the surface of a recess part 6b which is formed concavely on the top face of the cap body 6a and in which the needle attachment part 4a is to be fit. The cap body 6a is formed of elastomer similarly to the gasket body 2 described above, and the covering film 3 is formed of a PTFE film that is formed in the above method similarly to the one covering the gasket body 2.

By overlaying the covering film 3 on the superficial surface of the recess part 6b of the cap body 6a in the manner as described above, it is possible to make the needle attachment part 4a of the syringe barrel 4 fit in the recess part 6b of the top cap 6 smoothly, and to improve the liquid tightness and air tightness of the top cap 6 formed of elastomer.

Figure 2:
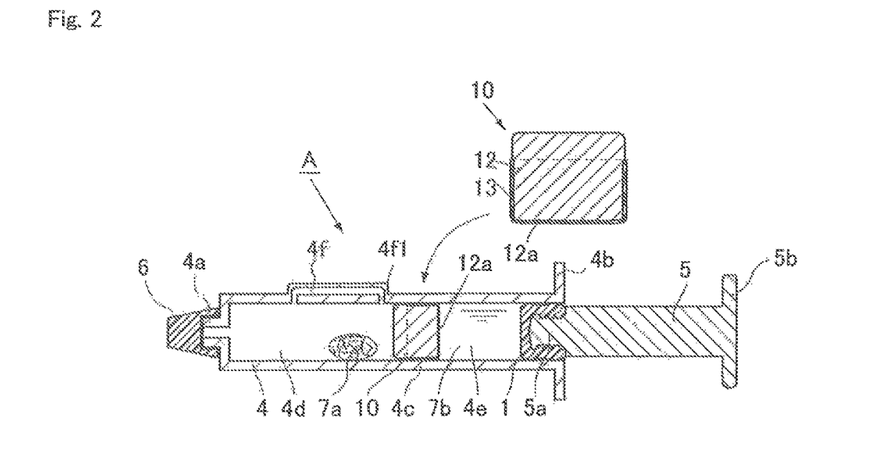
FIG. 2 is a cross-sectional view showing another example of the pre-filled syringe to which the present invention is applied.

FIG. 2 shows the case where an intermediate gasket 10 for syringe is used, and the intermediate gasket 10 is slidably accommodated in the syringe barrel 4. In a space 4d between the needle attachment part 4a of the syringe barrel 4 and the intermediate gasket 10, a solid agent 7a of, for example, powder of drug is stored, and a space 4e between the intermediate gasket 10 and the gasket 1 for piston is filled with pure water 7b. The outer wall of the space 4d for storage of solid agent is provided with a bypass canal 4f formed in the longitudinal direction of the syringe barrel 4. As the piston rod 5 is pushed in, the pure water 7b flows into the space 4d for storage of solid agent through the bypass canal 4f when the intermediate gasket 10 moves past an inlet 4f1 of the bypass canal 4f, and rapidly dissolves the solid agent 7a in the space 4d for storage of solid agent to give an injection liquid. In this case, as shown in the enlarged view of FIG. 2, the PTFE film 13 is attached to the intermediate gasket 10 to cover one end surface 12a and most of the circumferential face of the cylindrical gasket body 12, and the circumferential part is in slidable contact with the inner surface of the syringe barrel 4. The intermediate gasket 10 is disposed inside the syringe barrel 4 so that the end surface 12a on which the film is attached faces the pure water 7b. Although not shown in the drawing, a groove may be formed in the longitudinal direction in the inner wall in place of the external bypass canal 4f to function as a bypass, or although not shown in the drawing, both end surfaces of the intermediate gasket 10 and the circumferential face continuing to the both end surfaces may be covered with the PTFE film 13.

Focusing on the high barrier properties in a liquid contact surface with a drug liquid, the invention can be applied to plugs for medical purposes such as plugs of vials typically the gasket for syringe 1 and the top cap for syringe 6 configured as described above.

(Comparison in time-dependent change between results of a water vapor transmission measurement test for skived films according to the first and second methods of the present invention and a skived film subjected to a fusion treatment in atmospheric pressure without pressure reduction according to the conventional method: FIG. 3)

The transmission amount and its change of each PTFE film were determined in conformity with JIS Z-0208 (Testing Methods for Determination of the Water Vapor Transmission Rate of Moisture-proof Packaging Materials (Dish method)). According to FIG. 3, the inclination of the skived film (Sample A) obtained by the first method is smaller than that of the skived film formed by the conventional method (Comparative example), and the inclination of the skived film obtained by the second method becomes gentler as the pressurization force in the secondary thermal fusion treatment under increased pressure increases and approximates to that of a sample (Modified C4). Of course, when the pressuring force exceeds 5.0 MPa, the inclination becomes less than that of the sample (Modified C4), and the amount gradually decreases and converges to a certain value in the vicinity of the amount of the sample. Water vapor transmission rate (mg/m$^2$) per unit area after 24 hours is calculated from this graph and shown as water vapor transmission amount in FIG. 2 (the value obtained by dividing measurement of the moisture having passing through the skived film and absorbed in calcium chloride (anhydrous) by water vapor transmission area). The first and second skived films of the present invention are significantly improved in comparison with the comparative example (Unmodified/Comparative 1). As will be described later, the degree of pressure reduction during the primary thermal fusion is low, and the degree of pressurization during the secondary thermal fusion is high.

Table 1 shows comparison of treatment conditions, tensile elongation and tensile strength, water vapor transmission amount, and tear of film during injection in these films.

TABLE 1

| Sample No. | Pressure reduction (Pa) | Fusion temperature (° C.) | Fusion heating time | Pressurization (MPa) | Tensile elongation % Machine direction | Tensile elongation % Cross direction | Tensile strength N/mm$^2$ Machine direction | Tensile strength N/mm$^2$ Cross direction | Water vapor transmission amount mg/m$^2$ 24 hours | Tear of film during injection |
|---|---|---|---|---|---|---|---|---|---|---|
| Unmodified/Comparative 1 | 1 * 10$^5$ | 360 | 10 | — | 450 | 850 | 36.0 | 30.3 | 1500 | 50%× |
| Unmodified A1 | 13.30 | 360 | 10 | — | 507 | 920 | 41.7 | 36.1 | 372 | ○ |

TABLE 1-continued

| Sample No. | Pressure reduction (Pa) | Fusion temperature (° C.) | Fusion heating time | Pressurization (MPa) | Tensile elongation % Machine direction | Tensile elongation % Cross direction | Tensile strength N/mm² Machine direction | Tensile strength N/mm² Cross direction | Water vapor transmission amount mg/m² 24 hours | Tear of film during injection |
|---|---|---|---|---|---|---|---|---|---|---|
| Unmodified A2 | 0.13 | 360 | 10 | — | 526 | 963 | 40.1 | 36.9 | 353 | ○ |
| Unmodified A3 | 13.30 | 360 | 10 | 0.2 | 531 | 973 | 41.2 | 35.7 | 359 | ○ |
| Unmodified A4 | 13.30 | 360 | 10 | 5 | 554 | 970 | 41.1 | 34.6 | 248 | ○ |
| Unmodified A5 | 0.13 | 360 | 10 | 0.2 | 547 | 950 | 41.8 | 36.1 | 349 | ○ |
| Unmodified A6 | 0.13 | 360 | 10 | 5 | 551 | 958 | 41.4 | 35.9 | 238 | ○ |
| Modified B1 | 13.30 | 360 | 10 | — | 630 | 915 | 45.0 | 37.2 | 370 | ○ |
| Modified B2 | 0.13 | 360 | 10 | — | 641 | 955 | 46.9 | 38.8 | 340 | ○ |
| Modified B3 | 13.30 | 360 | 10 | 0.2 | 645 | 954 | 46.0 | 38.4 | 358 | ○ |
| Modified B4 | 13.30 | 360 | 10 | 0.6 | 649 | 955 | 46.0 | 38.3 | 235 | ○ |
| Modified B5 | 13.30 | 360 | 10 | 5 | 652 | 956 | 45.9 | 38.0 | 237 | ○ |
| Modified C1 | 0.13 | 360 | 10 | 0.2 | 619 | 932 | 44.8 | 37.1 | 243 | ○ |
| Modified C2 | 0.13 | 360 | 10 | 0.6 | 596 | 947 | 43.8 | 36.7 | 221 | ○ |
| Modified C3 | 0.13 | 360 | 10 | 5 | 628 | 954 | 43.5 | 36.4 | 219 | ○ |

"Unmodified/Comparative 1" is a comparative example of an unmodified PTFE skived film without pressure reduction and pressurization.

"Unmodified A1" and "Unmodified A2" are examples of unmodified PTFE skived films with pressure reduction and without pressurization (first method).

"Unmodified A3" to "Unmodified A6" are examples of unmodified PTFE skived films with pressure reduction and pressurization (second method).

"Modified B1" and "Modified B2" are examples of modified PTFE skived films with pressure reduction and without pressurization (first method).

"Modified B3" to "Modified B5" and "Modified C1" to "Modified C3" are examples of modified PTFE skived films with pressure reduction and pressurization (second method).

"Pressure reduction" represents degree of pressure reduction in the furnace during thermal fusion.

"$1 \times 10^5$" represents atmospheric pressure.

"Pressurization" represents pressure in the furnace during secondary thermal fusion in the second method.

"Water vapor transmission amount" represents the amount of water vapor transmission per unit area after a lapse of 24 hours from starting of the experiment.

The gasket body subjected to injection has a diameter of 5 mm and a length of 5 mm, and the skived film used in the experiment has a thickness of 100 μm. "×" indicates that film tear was observed, and "○" indicates that film tear was not observed.

According to Table 1, "Unmodified/Comparative 1" in which unmodified PTFE was used and thermal fusion was conducted at normal pressure ($1 \times 10^5$ Pa) exhibits a large water vapor transmission amount and causes film tear during injection molding.

On the other hand, in "Unmodified A1" and "Unmodified A2" in which unmodified PTFE was used and thermal fusion was conducted under reduced pressure of 0.013 Pa or 133 Pa according to the first method, the water vapor transmission amount was dramatically reduced by virtue of the thermal fusion treatment under reduced pressure, and film tear was not observed during injection molding owing to improved elongation. In the second method in which pressurization is added, further improvement was observed. When modified PTFE is used, these points are further improved. In other words, these seem to be gradually converged and improved as the pressure reduction degree (or pressure reduction degree during primary fusion) is decreased, and the pressurization degree during the secondary fusion is increased. FIG. 3 shows data shown in Table 1 selectively.

DESCRIPTION OF THE REFERENCE CHARACTERS

A pre-filled syringe
1 gasket for syringe
2 gasket body
3 gasket covering film
4 syringe barrel
5 piston rod
6 top cap for syringe
7 drug liquid

The invention claimed is:
1. A method for producing a polytetrafluoroethylene film for covering a surface of a plug for medical purposes, comprising the steps of:
   pressure-molding powder material of polytetrafluoroethylene or modified polytetrafluoroethylene charged in a mold to obtain a pressure-molded product having interconnected cells inside;
   subjecting the pressure-molded product obtained by the pressure molding to a thermal fusion treatment under reduced pressure; and cutting the product subjected to the thermal fusion treatment obtained by the thermal fusion treatment to obtain a film.

2. The method of claim 1, wherein the thermal fusion treatment comprising the steps of:
   subjecting the pressure-molded product to a primary thermal fusion treatment under reduced pressure to block outlets of communication holes of the pressure-molded product to obtain a product subjected to the primary thermal fusion treatment including only closed cells remaining inside; and
   subjecting the product subjected to the primary thermal fusion treatment to a secondary thermal fusion treatment under increased pressure to obtain a product subjected to the secondary thermal fusion treatment from which the closed cells have disappeared.

3. The method of claim 1, wherein the powder material of polytetrafluoroethylene or modified polytetrafluoroethylene charged in the mold is pressure-molded under reduced pressure to obtain a pressure-molded product.

4. The method of claim 1 wherein pressure reduction is conducted within a pressure range of 0.013 to 133 Pa.

5. The method of claim 1, wherein a thermal fusion treatment temperature is 320 to 400° C.

6. The method of claim 1, wherein the product subjected to the thermal fusion treatment has a shape which is a rectangular parallelepiped, a cube, a circular column, or a cylinder.

7. The method of claim 1, wherein the film produced by cutting the product subjected to the thermal fusion treatment has a thickness ranging from 20 to 150 μm.

8. The method of claim 2, wherein a range of pressurization pressure in the secondary thermal fusion treatment is higher than or equal to 0.2 Ma.

* * * * *